United States Patent [19]

Hesse

[11] Patent Number: Plant 6,330

[45] Date of Patent: Oct. 11, 1988

[54] CHRYSANTHEMUM PLANT NAMED LAMPLIGHT

[75] Inventor: Peter S. Hesse, Bradenton, Fla.

[73] Assignee: Ball Pan Am Plant Company, Parrish, Fla.

[21] Appl. No.: 927,121

[22] Filed: Nov. 5, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Lamplight particularly characterized by its flat capitulum form and single capitulum type, light bronze ray florets, rich yellow mature disc florets, eight week flowering response, and by its excellent flower substance and good keeping quality.

1 Drawing Sheet

The present invention comprises a new and distinct cultivar of Chrysanthemum, botanically known as *Chrysanthemum morifolium,* Ramat., and referred to by the cultivar name Lamplight.

Lamplight is a product of a planned breeding program which had the objective of creating new Chrysanthemum cultivars with an eight week flowering response, bronze color, daisy type flowers, good flower substance, and good keeping quality. Such traits in combination were not present or were in need of improvement in previously available commercial cultivars.

Lamplight was originated from a hybridization made by applicant in a controlled breeding program in West Chicago, Ill. in 1980. The female parent was Twilight, a commercially known and patented cultivar. The male parent of Lamplight was Circus, also a commercially known and patented cultivar.

Lamplight was discovered and selected as one flowering plant within the progeny of the stated parentage by Peter S. Hesse in November 1981 in a controlled environment in Parrish, Fla.

The first act of asexual reproduction of Lamplight was accomplished when vegetative cuttings were taken from the initial selection in February 1982 in a controlled environment in Parrish, Fla. by a technician working under formulations established and supervised by Peter S. Hesse. Horticultural examination of selected units initiated in 1982 has demonstrated that the combination of characteristics as herein disclosed for Lamplight are firmly fixed and are retained through successive generations of asexual reproduction.

Lamplight has not been observed under all possible environmental conditions. The phenotype may vary significantly with variations in environment such as temperature, light intensity and day length. The following observations, measurements and comparisons describe plants grown in Parrish, Fla. under greenhouse conditions which approximate those generally used in commercial practice.

The following traits have been repeatedly observed and are determined to be basic characteristics of Lamplight, which in combination distinguish this Chrysanthemum as a new and distinct cultivar:

1. Eight week response period.
2. Flat capitulum form, single capitulum type.
3. Butterscotch bronze color of ray florets.
4. The under surface of the ray florets is a bicolored golden yellow/butterscotch.

5. Disc florets are a rich yellow when mature, shedding little pollen; immature disc florets are lime green.
6. Capitulum 5 to 6 cm across; mature ray florets 18–22 mm long, 10 mm across, approximately 21 ray florets per flower.
7. Each plant produces 4–5 breaks after pinching.
8. Leaves are of medium size, up to 110 mm long and 70 mm wide.
9. Plant is of medium height, growing approximately 30 cm above the edge of the pot when grown under a normal pot mum program.
10. Excellent flower substance and good keeping quality.

Of the many commercial cultivars known to the present inventor, the most similar in comparison to Lamplight are Candlelight and Cirbronze. Reference is made to attached Chart A which compares certain characteristics of Lamplight to those same characteristics of Cirbronze. Compared to Cirbronze, Lamplight has slightly smaller flowers, fewer ray florets, a lighter flower color, and a slightly more vigorous growth habit. In comparison to Candlelight, Lamplight has a more compact habit, earlier flowering response (8 weeks vs. 10 weeks), and more resistance to heat delay. The flower form and type, and flower color of Lamplight are similar to those same characteristics of Candlelight.

The accompanying photographic drawing shows typical inflorescence and foliage characteristics of Lamplight, with colors being as nearly true as possible with illustrations of this type. The drawing comprises a black and white photograph in which several flowers appear in color to accurately represent ray and disc floret color.

In the following description, color references are made to The Royal Horticultural Society Colour Chart. The color values were taken at approximately 12:00 noon on July 21, 1986 under florescent light at Parrish, Fla.

Classification:

*Botanical: Chrysanthemum morifolium,* Ramat., cv. Lamplight

*Commercial:* Daisy pot mum.

INFLORESCENCE

A. Capitulum:

*Form.*—Flat.

*Type.*—Single.

*Diameter across face.*—50–60 mm.

B. Corolla of ray florets:

*Color (general tonality from a distance of three meters).*—Light bronze.

*Color (upper surface).*—163B.

*Color (under surface).*—bi-colored 163A and 12B.

C. Corolla of disc florets:

*Color (mature).*—Deep yellow.

*Color (immature).*—Light green.

D. Reproductive organs:

*Androecium.*—Present in disc florets only.

*Gynoecium.*—Present in both ray and disc florets.

PLANT

A. General appearance:

*Height.*—28–32 cm above the edge of the pot.

B. Foliage:

*Color (upper surface).*—147A.

*Color (under surface).*—147B.

*Shape.*—Generally ovate, deeply lobed and serrated.

CHART A

| | Cirbronze vs. Lamplight Summer Conditions | |
|---|---|---|
| | Cirbronze | Lamplight |
| Flower Diameter | up to 60 mm | up to 55 mm |
| Ray Floret Number | average 29 | average 22 |
| Mature Flower Color | 166D | 9B |
| Immature Flower Color | 178C | 167C |

The plants of Cirbronze and Lamplight which were used in this comparison were grown together on the same bench in a greenhouse in Parrish, Fla. The color readings were taken under fluorescent light at 11:00 a.m. on Sept. 12, 1986.

Lamplight in comparison to Cirbronze has slightly smaller flowers, less ray florets, lighter flower color and a slightly more vigorous growth habit under Florida summer conditions.

I claim:

1. A new and distinct cultivar of Chrysanthemum named Lamplight, as described and illustrated, and particularly characterized by its flat capitulum form and single capitulum type, light bronze ray florets, rich yellow mature disc florets, eight week flowering response, and excellent flower substance and good keeping quality.

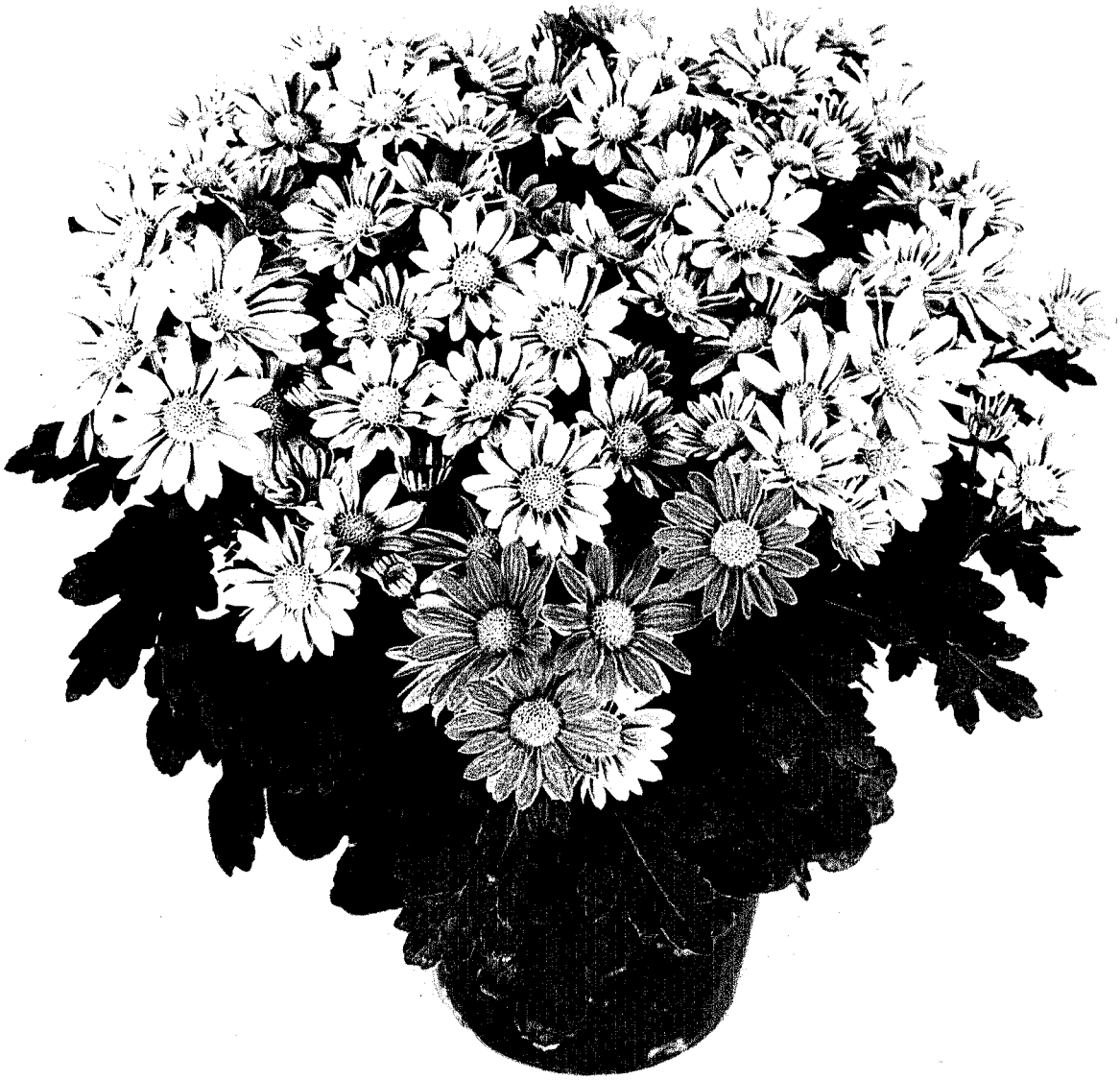

* * * * *